(12) United States Patent
Peterson

(10) Patent No.: US 8,598,841 B2
(45) Date of Patent: *Dec. 3, 2013

(54) CHARGER ALIGNMENT INDICATOR WITH ADJUSTABLE THRESHOLD

(75) Inventor: David K. L. Peterson, Saugus, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 148 days.

This patent is subject to a terminal disclaimer.

(21) Appl. No.: 13/247,642

(22) Filed: Sep. 28, 2011

(65) Prior Publication Data

US 2012/0019201 A1    Jan. 26, 2012

Related U.S. Application Data

(63) Continuation of application No. 13/053,998, filed on Mar. 22, 2011, now Pat. No. 8,044,635, and a continuation of application No. 11/748,436, filed on May 14, 2007, now Pat. No. 7,932,696.

(51) Int. Cl.
    *H01M 10/46*    (2006.01)
(52) U.S. Cl.
    USPC .......................................................... 320/114
(58) Field of Classification Search
    USPC .............. 320/107, 108, 112, 114, 115, 141; 607/27, 29, 33
    See application file for complete search history.

(56) References Cited

U.S. PATENT DOCUMENTS

| | | | |
|---|---|---|---|
| 3,646,940 A | 3/1972 | Timm et al. | |
| 3,822,708 A | 7/1974 | Zilber | |
| 5,690,693 A | 11/1997 | Wang et al. | |
| 6,194,874 B1 | 2/2001 | Kalogeropoulos et al. | |
| 6,516,227 B1 | 2/2003 | Meadows et al. | |
| 6,594,524 B2 | 7/2003 | Esteller et al. | |
| 8,044,635 B2 * | 10/2011 | Peterson | 320/114 |
| 2003/0195581 A1 | 10/2003 | Meadows et al. | |
| 2005/0075699 A1 | 4/2005 | Olson et al. | |
| 2005/0192504 A1 | 9/2005 | Palreddy et al. | |
| 2006/0247737 A1 | 11/2006 | Olson et al. | |
| 2007/0185551 A1 | 8/2007 | Meadows et al. | |
| 2008/0288025 A1 | 11/2008 | Peterson | |

FOREIGN PATENT DOCUMENTS

| | | |
|---|---|---|
| EP | 1 136 098 A2 | 9/2001 |
| EP | 1 136 098 A3 | 7/2003 |
| JP | A-H11-506646 A | 6/1999 |
| JP | 2000111315 A | 4/2000 |
| WO | WO 98/11942 A1 | 3/1998 |

OTHER PUBLICATIONS

PCT International Search Report for PCT/US2008/006129, Applicant: Boston Scientific Neuromodulation Corporation, Form PCT/ISA/210 and 220, dated Sep. 9, 2008 (6 pages).

(Continued)

*Primary Examiner* — Edward Tso
(74) *Attorney, Agent, or Firm* — Vista IP Law Group LLP

(57) ABSTRACT

Electrical energy is transmitted to charge the implanted medical device, and an electrical parameter (e.g., a steady-state voltage) indicating a rate at which the implanted medical device is charged by the electrical energy is detected. A threshold (e.g., by modifying a stored threshold value) at which the charge strength indicator generates a user-discernible signal is adjusted based on the detected electrical parameter.

26 Claims, 5 Drawing Sheets

(56) References Cited

OTHER PUBLICATIONS

PCT Written Opinion of the International Search Authority for PCT/US2008/006129, Applicant: Boston Scientific Neuromodulation Corporation, Form PCT/ISA/237, dated Sep. 9, 2008 (7 pages).
EP Office Action dated Apr. 27, 2010 in related European Patent Application No. 08767685.4-2305, Applicant: Boston Scientific Neuromodulation Corporation, (5 pages).
EP Office Action dated Oct. 1, 2010 in related European Patent Application No. 08767685.4-2305, Applicant: Boston Scientific Neuromodulation Corporation, (4 pages).
PCT International Preliminary Report on Patentability (Ch. 1 of the Patent Cooperation Treaty) for PCT/US2008/006129, Applicant: Boston Scientific Neuromodulation Corporation, Form PCT/IB/326 and 373, dated Nov. 26, 2009 (9 pages).
The extended European search report dated Aug. 7, 2012 in European Patent Application Serial No. 12167016.0-2305, Applicant: Boston Scientific Neuromodulation Corporation, (6pages).
JP Office Action dated Jun. 26, 2013 in Japanese Application Serial No. 2010-508404, Applicant: Boston Scientific Neuromodulation Corporation, (3pages) including an English Translation prepare by Nakamura & Partners (4pages).
JP Office Action dated Oct. 26, 2012 in related Japanese Patent Application No. 2010-508404, Applicant: Boston Scientific Neuromodulation Corporation, (2pages); English Translations provided by the Nakamura & Partners (2pages).
CA Office Action dated Dec. 17, 2012 in related Canadian Patent Application No. 2,684,995, Applicant: Boston Scientific Neuromodulation Corporation, (2pages).

\* cited by examiner

CHARGER ALIGNMENT INDICATOR WITH ADJUSTABLE THRESHOLD

RELATED APPLICATIONS

The present application is a continuation of U.S. patent application Ser. No. 13/053,998, which is a continuation of U.S. patent application Ser. No. 11/748,436, filed May 14, 2007, which applications are expressly incorporated herein by reference.

FIELD OF THE INVENTION

The present invention relates to implantable devices, and more particularly, to devices for transcutaneously recharging devices implanted within patients.

BACKGROUND OF THE INVENTION

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a spinal cord stimulation system, such as that disclosed in U.S. Pat. No. 6,516,227 ("the '227 patent"), issued Feb. 4, 2003 in the name of inventors Paul Meadows et al., which is incorporated herein by reference in its entirety.

Spinal cord stimulation is a well-accepted clinical method for reducing pain of certain populations of patients. A spinal cord stimulation (SCS) system typically includes an implantable pulse generator and at least one stimulation electrode lead that carries electrodes that are arranged in a desired pattern and spacing to create an electrode array. Individual wires within the electrode lead(s) connect with each electrode in the array. The electrode lead(s) is typically implanted along the dura of the spinal cord, with the electrode lead(s) exiting the spinal column, where it can generally be coupled to one or more electrode lead extensions. The electrode lead extension(s), in turn, are typically tunneled around the torso of the patient to a subcutaneous pocket where the implantable pulse generator is implanted. Alternatively, the electrode(s) lead may be directly coupled to the implantable pulse generator. For examples of other SCS systems and other stimulation systems, see U.S. Pat. Nos. 3,646,940 and 3,822,708, which are hereby incorporated by reference in their entireties.

Of course, implantable pulse generators are active devices requiring energy for operation. Oftentimes, it is desirable to recharge an implanted pulse generator via an external charger, so that a surgical procedure to replace a power depleted implantable pulse generator can be avoided. To wirelessly convey energy between the external charger and the implanted pulse generator, the recharger typically includes an alternating current (AC) charging coil that supplies energy to a similar charging coil located in or on the implantable pulse generator. The energy received by the charging coil located on the implantable pulse generator can then be used to directly power the electronic componentry contained within the pulse generator, or can be stored in a rechargeable battery within the pulse generator, which can then be used to power the electronic componentry on-demand.

To provide efficient power transmission through tissue from the external charger to the implanted pulse generator, it is paramount that the charging coil located in or on the implantable pulse generator be spatially arranged relative to the corresponding AC coil of the external charger in a suitable manner. That is, efficient power transmission through the patient's skin from the external charger to the implantable pulse generator via inductive coupling requires constant close alignment between the two devices. To ensure that such constant close alignment is achieved, the external charger typically includes an alignment indicator that provides a visual or audible signal that can be used by the patient to reposition or reorient the external charger, thereby maintaining or optimizing the rate at which the implantable pulse generator is charged.

One known approach is to use a charge strength indicator on the external charger to indicate the extent of the charge rate. For example, a bar charge indicator can be used, such that one bar indicates a relatively low charge rate, two bars indicate a greater charge rate, three bars indicate an even greater charge rate, and so forth. One downfall of using a bar charge connection indicator is that the patient must continually looks at the indicator to ensure an optimal charge rate.

Another approach is to use a misalignment indicator on the external charger that signals to the patient with an audible misalignment tone whenever the charge rate falls below the optimal level. However, this approach currently limits the possibility of charging more deeply implanted pulse generators at lower rates without inadvertently triggering the misalignment tone. Although the alignment zone of the external charger could be expanded to prevent such inadvertent triggering of the misalignment tone, the indicator may not generate the misalignment tone when the charge rate actually is less than optimal. Thus, the patient may charge the implantable pulse generator at a sub-optimal rate without ever being warned.

An external charger that combines both a bar charge indicator and a misalignment indicator would still require the patient to monitor the bar charge indicator during charging or endure an audible tone that inappropriately signals for deeper implantable pulse generators. There, thus, remains a need for an improved method and system for indicating alignment or misalignment between an external charger and an implantable pulse generator.

SUMMARY OF THE INVENTION

In accordance with a first aspect of the present invention, a method of adjusting a charge strength indicator for an implanted medical device (e.g., a neurostimulation device) is provided. In one embodiment, the charge strength indicator may be located on an external charger, although in other embodiments, the charge strength indicator may be located on other devices, such as the implanted medical device, itself. The method comprises transcutaneously transmitting electrical energy to charge the implanted medical device, and detecting an electrical parameter (e.g., a steady-state voltage). In one method, the electrical parameter indicates a rate at which the implanted medical device is charged by the electrical energy. The method further comprises adjusting a threshold (e.g., by modifying a stored threshold value) at which the charge strength indicator generates a user-discernible signal based on the detected electrical parameter. In one method, the user-discernible signal is binary signal; for example, an audible signal that indicates whether or not a misalignment condition has occurred. Although the broadest aspects of the present inventions should not be so limited, adjustment of the threshold allows the charge strength indicator to be tailored to the patient and at the particular depth of the implanted medical device, so that the user-discernible signal is generated at the intended times.

The threshold may be adjusted in any one of a variety of manners. For example, the threshold can be manually adjusted (e.g., by setting a threshold value in accordance with the depth at which the medical device is implanted). Or the threshold can be automatically adjusted in response to the detection of the electrical parameter. Or the threshold can be adjusted based only on a currently detected electrical parameter (e.g., by modifying a threshold value to equal the value of the currently detected electrical parameter).

In one advantageous method, the electrical energy is transcutaneously conveyed repeatedly over a series of discrete time periods to charge the implanted medical device, the electrical parameter is detected during the discrete time periods, and the threshold is adjusted based on the detected electrical parameter during the discrete time periods. As examples, the value of the detected electrical parameter indicating the maximum charge rate can be determined during the discrete time periods, or the value of the detected electrical parameter indicating the most common charge rate can be determined during the discrete time periods. The threshold can then be adjusted based on the determined electrical parameter value (e.g., by automatically setting a threshold value to the determined electrical parameter value). If the value of the detected electrical parameter indicating the most common charge rate is determined, an electrical parameter histogram can be generated over the discrete time periods, so that the value of the detected electrical parameter can be selected from the histogram.

In accordance with a second aspect of the present invention, an implantable medical system is provided. The medical system comprises an implantable medical device (e.g., a neurostimulation device) and an external charger configured for transcutaneously conveying electrical energy to charge the implanted medical device. The medical system further comprises a charge strength indicator configured for generating a user-discernible signal, a detector configured for detecting an electrical parameter (e.g., a stead-state charging voltage). The electrical parameter may indicate a rate at which the implanted medical device is charged by the electrical energy. The medical system further comprises a processor configured for adjusting a threshold at which the charge strength indicator generates a user-discernible signal based on the detected electrical parameter.

In one embodiment, the indicator, detector, and processor are contained within the external charger, although in other embodiments, any one or more of the indicator, detector, and processor, can be contained in another device, such as the medical device, itself. In another embodiment, the indicator is a binary indicator; for example, an audio transducer that indicates whether or not a misalignment condition has occurred. An optional embodiment comprises memory configured for storing a threshold value, in which case, the processor is configured for adjusting the threshold by modifying the stored threshold value. The processor can modify the threshold in any one of the manners discussed above.

In accordance with a third aspect of the present inventions, an external charger for an implantable medical device is provided. The external charger comprises a source of electrical power (e.g., a battery), an alternating current (AC) coil configured for transcutaneously conveying electrical energy from the electrical power source to charge the implanted medical device, and a charge strength indicator configured for generating a user-discernible signal. The external charger further comprises a detector configured for detecting an electrical parameter (e.g., a stead-state voltage). The electrical parameter may indicate a rate at which the implanted medical device is charged by the electrical energy. The external charger further comprises a processor configured for adjusting a threshold at which the charge strength indicator generates a user-discernible signal based on the detected electrical parameter.

In one embodiment, the external charger comprises a portable housing containing the electrical power source, AC coil, indicator, detector, and processor. In another embodiment, the indicator is a binary indicator; for example, an audio transducer that indicates whether or not a misalignment condition has occurred. An optional embodiment comprises memory configured for storing a threshold value, in which case, the processor is configured for adjusting the threshold by modifying the stored threshold value. The processor can modify the threshold in any one of the manners discussed above.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG) or similar electrical stimulator, which may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited.

Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical and deep brain stimulator, peripheral nerve stimulator, or in any other neural stimulator configured to treat urinary incontinence, sleep apnea, shoulder sublaxation, etc.

Figure 1:
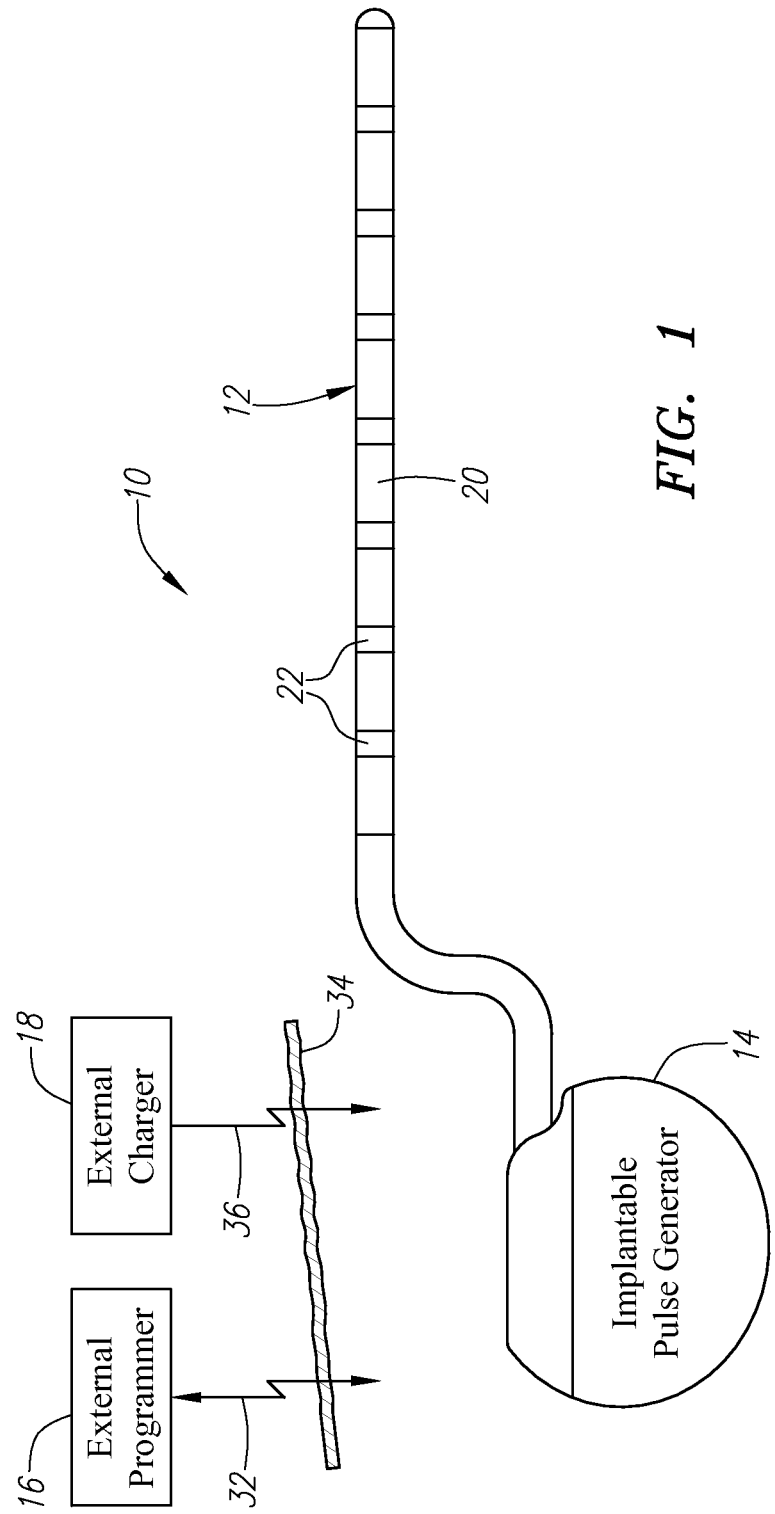
FIG. 1 is plan view of one embodiment of a spinal cord stimulation (SCS) system arranged in accordance with the present inventions.

Turning first to FIG. 1, an exemplary SCS system 10 generally an implantable neurostimulation lead 12, an implantable pulse generator (IPG) 14, an external (non-implanted) programmer 16, and an external (non-implanted) charger 18. In the illustrated embodiment, the lead 12 is a percutaneous lead and, to that end, includes a plurality of in-line electrodes 20 carried on a flexible body 22. Alternatively, the lead 12 may take the form of a paddle lead. The IPG 14 is electrically coupled to the lead 12 in order to direct electrical stimulation energy to each of the electrodes 20. The IPG 14 includes an outer case formed from an electrically conductive, biocompatible material, such as titanium and, in some instances, will function as an electrode. The case forms a hermetically sealed compartment wherein the electronic and other components are protected from the body tissue and fluids. For purposes of brevity, the electronic components of the IPG 14, with the exception of the components needed to facilitate the recharging function (described below), will not be described herein. Details of the IPG 14, including the battery, antenna coil, and telemetry and charging circuitry, are disclosed in U.S. Pat. No. 6,516,227, which is expressly incorporated herein by reference.

Figure 2:
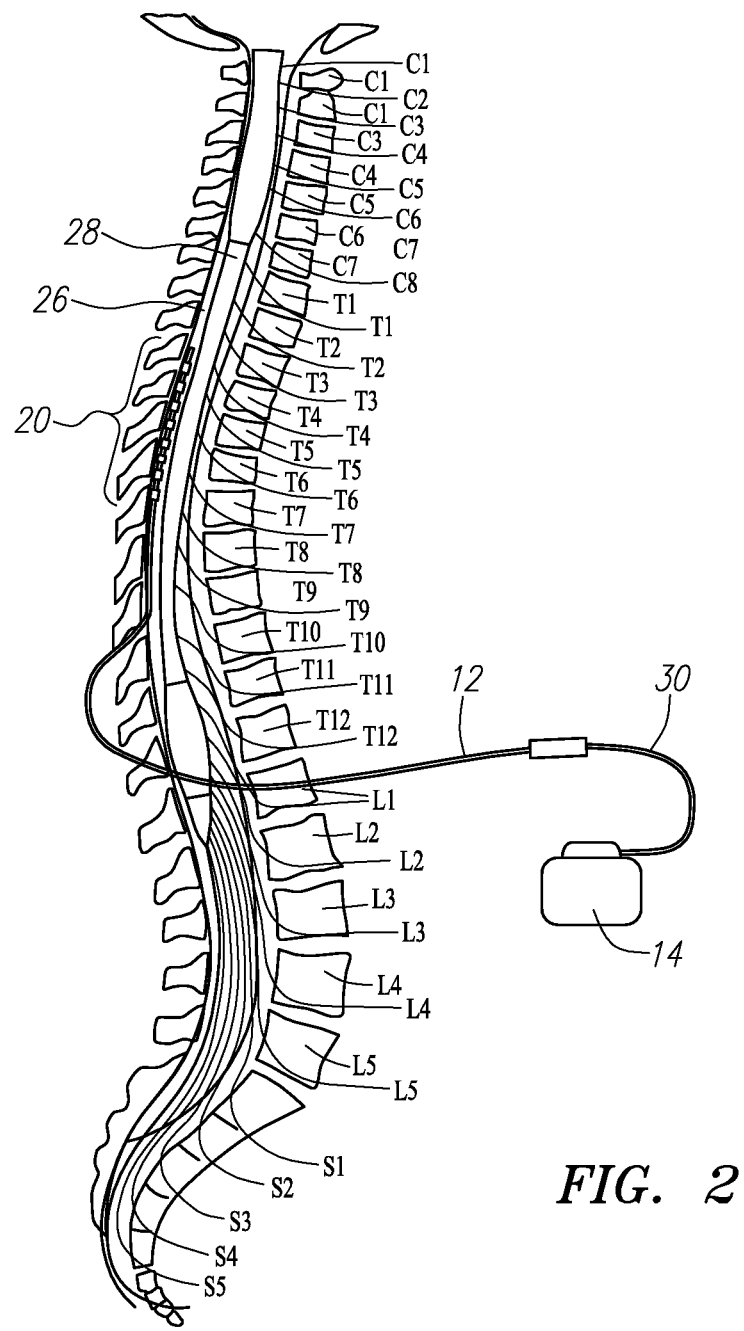
FIG. 2 is a plan view of the SCS system of FIG. 1 in use with a patient.

As shown in FIG. 2, the neurostimulation lead 12 is implanted within the epidural space 26 of a patient through the use of a percutaneous needle or other convention technique, so as to be in close proximity to the spinal cord 28. Once in place, the electrodes 20 may be used to supply stimulation energy to the spinal cord 28 or nerve roots. The preferred placement of the lead 12 is such, that the electrodes 20 are adjacent, i.e., resting upon, the nerve area to be stimulated. Due to the lack of space near the location where the lead 12 exits the epidural space 26, the IPG 14 is generally implanted in a surgically-made pocket either in the abdomen or above the buttocks. The IPG 14 may, of course, also be implanted in other locations of the patient's body. A lead extension 30 may facilitate locating the IPG 14 away from the exit point of the lead 12.

Referring back to FIG. 1, the IPG 14 is programmed, or controlled, through the use of the external programmer 18. The external programmer 18 is transcutaneously coupled to the IPG 14 through a suitable communications link (represented by the arrow 32) that passes through the patient's skin 34. Suitable links include, but are not limited to radio frequency (RF) links, inductive links, optical links, and magnetic links. For purposes of brevity, the electronic components of the external programmer 18 will not be described herein. Details of the external programmer, including the control circuitry, processing circuitry, and telemetry circuitry, are disclosed in U.S. Pat. No. 6,516,227, which has been previously incorporated herein by reference.

The external charger 18 is transcutaneously coupled to the IPG 14 through a suitable link (represented by the arrow 36) that passes through the patient's skin 34, thereby coupling power into the IPG 14 for the purpose of operating the IPG 14 or replenishing a power source, such as a rechargeable battery (e.g., a Lithium Ion battery), within the IPG 14. In the illustrated embodiment, the link 36 is an inductive link; that is, energy from the external charger 18 is coupled to the battery within the IPG 14 via electromagnetic coupling. Once power is induced in the charging coil in the IPG 14, charge control circuitry within the IPG 14 provides the power charging protocol to charge the battery. As will be described in further detail below, the external charger 18 generates an audible tone when misaligned with the IPG 14 to alert the user to adjust the positioning of the external charger 18 relative to the IPG 14. The external charger 18 is designed to charge the battery of the IPG 14 to 80% capacity in two hours, and to 100% in three hours, at implant depths of up to 2.5 cm. When charging is complete, the external charger 18 generates an audible tone to alert the user to decouple the external charger 18 from the IPG 14.

Once the IPG 14 has been programmed, and its power source has been charged or otherwise replenished, the IPG 14 may function as programmed without the external programmer 16 being present. While the external programmer 16 and external charger 18 are described herein as two separate and distinct units, it should be appreciated that the functionality of the external programmer 16 and external charger 18 can be combined into a single unit. It should be noted that rather than an IPG, the SCS system 10 may alternatively utilize an implantable receiver-stimulator (not shown) connected to leads 12, 14. In this case, the power source, e.g., a battery, for powering the implanted receiver, as well as control circuitry to command the receiver-stimulator, will be contained in an external controller/charger inductively coupled to the receiver-stimulator via an electromagnetic link.

Figure 3:
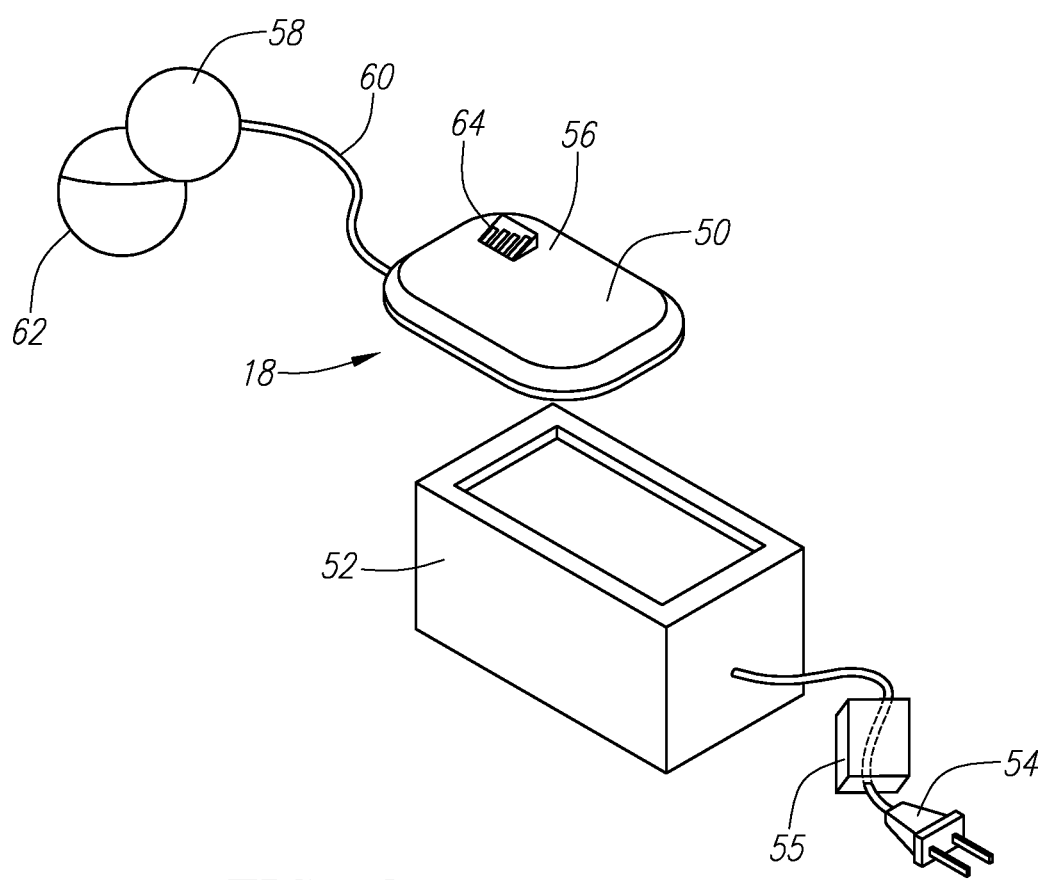
FIG. 3 is a perspective view of one embodiment of an external charger used in the SCS system of FIG. 1.

Referring now to FIG. 3, the external components of the external charger 18 will be described. In this embodiment, the external charger 18 takes the form of a two-part system comprising a portable charger 50 and a charging base station 52. The charging base station 52 includes an AC plug 54, so that it can be easily plugged into any standard 110 volt alternating current (VAC) or 200 VAC outlet. The charging base station 52 further includes an AC/DC transformer 55, which provides a suitable DC voltage (e.g., 5 VDC) to the circuitry within the charging base station 52.

The portable charger 50 includes a housing 56 for containing circuitry, and in particular, the recharging circuitry and battery (not shown in FIG. 3), which will be discussed in further detail below. The housing 56 is shaped and designed in a manner that allows the portable charger 50 to be detachably inserted into the charging base station 52, thereby allowing the portable charger 50, itself, to be recharged. Thus, both the IPG 14 and the portable charger 50 are rechargeable. The portable charger 50 may be returned to the charging base station 52 between uses.

In the illustrated embodiment, the portable charger 50 includes a charging head 58 connected to the housing 56 by way of a suitable flexible cable 60. The charging head 58 houses the AC coil (not shown in FIG. 3) from which the charging energy is transmitted. The portable charger 50 further includes a disposable adhesive pouch 62 or Velcro® strip or patch, which may be placed on the patient's skin over the location where the IPG 14 is implanted. Thus, the charging head 58 may be simply slid into the pouch 62, or fastened to the strip or patch, so that it can be located in proximity to the IPG 14 (e.g., 2-3 cm). In an alternative embodiment, the portable charger 50 does not include a separate charging head, but instead includes a single housing that contains the recharging circuitry, battery, and AC coil.

In order for efficient transfer of energy to the IPG 14, it is important that the charging head 58 (or more particularly, the AC coil within the head 58) be properly aligned with the IPG 14. Thus, in the illustrated embodiment, the portable charger 50 includes a bar charge indicator 64 located on the housing 56, which provides a visual indication of the strength of the charging between the charging head 58 and IPG 14 in the form of bars. As will be described in further detail below, the portable charger 50 comprises a misalignment indicator in the form of an audio transducer that provides an audible indication when the charging head 58 is misaligned relative to the IPG 14. For the purposes of this specification, both the bar charge indicator 64 and misalignment indicator can be considered as charge strength indicators. Once proper alignment with the IPG 14 has been achieved, as indicated by the bar charge indicator 64 or misalignment indicator, the housing 56 may simply be taped in place on the patient's skin using removable medical tape. Typically, charging of the IPG 14 continues until the battery of the IPG 14 has been charged to at least 80% of capacity.

Figure 4:
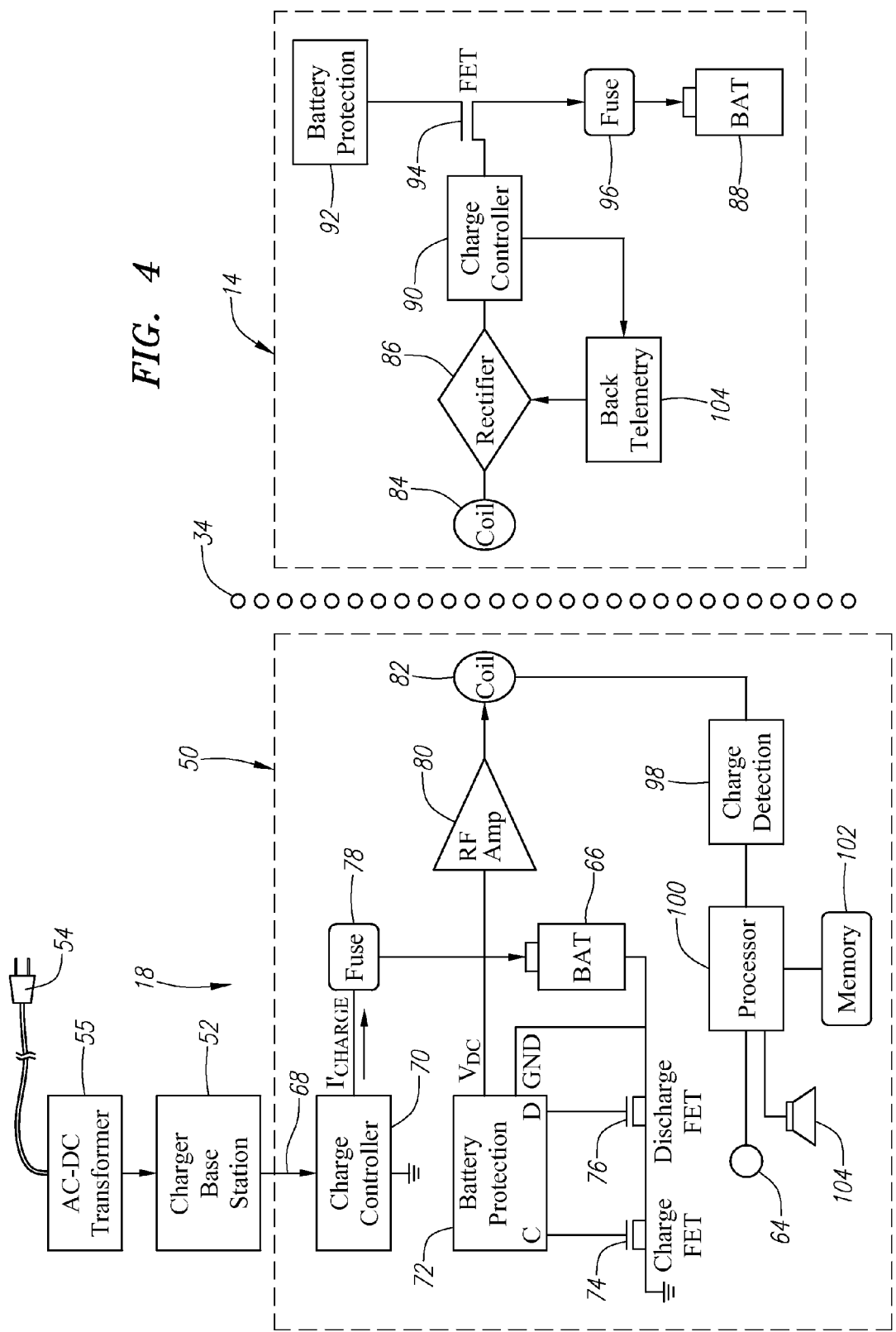
FIG. 4 is a block diagram of the internal components of one embodiment of an external charger and implantable pulse generator used in the SCS system of FIG. 1.

Referring to FIG. 4, the recharging elements of the IPG 14 and portable charger 50 will now be described. It should be noted that the diagram of FIG. 4 is functional only, and is not intended to be limiting. Those of skill in the art, given the descriptions presented herein, should be able to readily fashion numerous types of recharging circuits, or equivalent circuits, that carry out the functions indicated and described.

As previously discussed above, the external charger 18 and IPG 14 are shown inductively coupled together through the patient's skin 34 (shown by dotted line) via the inductive link 36 (shown by wavy arrow). The portable charger 50 includes a battery 66, which in the illustrated embodiment is a rechargeable battery, such as a Lithium Ion battery. Thus, when a recharge is needed, energy (shown by arrow 68) is coupled to the battery 66 via the charging base station 52 in a conventional manner. In the illustrated embodiment, the battery 66 is fully charged in approximately four hours. Once the battery 66 is fully charged, it has enough energy to fully recharge the battery of the IPG 14. If the portable charger 50 is not used and left on charger base station 52, the battery 66 will self-discharge at a rate of about 10% per month. Alternatively, the battery 66 may be a replaceable battery.

The portable charger 50 includes a charge controller 70, which serves to convert the DC power from the AC/DC transformer 55 to the proper charge current and voltage for the battery 66, a battery protection circuit 72, which monitors the voltage and current of the battery 66 to ensure safe operation via operation of FET switches 74, 76, and a fuse 78 that disconnects the battery 66 in response to an excessive current condition that occurs over an extended period of time. Further details discussing this control and protection circuitry are described in U.S. Pat. No. 6,516,227, which has been previously incorporated herein by reference.

The portable charger 50 further includes a power amplifier 80, and in particular a radio frequency (RF) amplifier, for converting the DC power from the battery 66 to a large alternating current. The power amplifier may take the form of an E-class amplifier. The portable charger 50 further includes an antenna 82, and in particular a coil, configured for transmitting the alternating current to the IPG 14 via inductive coupling. The coil 82 may comprise a 36 turn, single layer, 30 AWG copper air-core coil having a typical inductance of 45 µH and a DC resistance of about 1.15Ω. The coil 82 may be tuned for a resonance at 80 KHz with a parallel capacitor (not shown).

The IPG 14 includes an antenna 84, and in particular a coil, configured for receiving the alternating current from the portable charger 50 via the inductive coupling. The coil 84 may be identical to, and preferably has the same resonant frequency as, the coil 82 of the portable charger 50. The IPG 14 further comprises rectifier circuitry 86 for converting the alternating current back to DC power. The rectifier circuitry 86 may, e.g., take the form of a bridge rectifier circuit. The IPG 14 further includes a rechargeable battery 88, such as a Lithium Ion battery, which is charged by the DC power output by the rectifier circuitry 86. In the illustrated embodiment, the battery 88 can be fully charged by the portable charger 50 in under three hours (80% charge in two hours).

The portable charger 50 includes a charge controller 90, which serves to convert the DC power from the rectifier circuitry 86 to the proper charge current and voltage for the battery 88, a battery protection circuit 92, which monitors the voltage and current of the battery 88 to ensure safe operation via operation of a FET switch 94, and a fuse 96 that disconnects the battery 88 in response to an excessive current condition that occurs over an extended period of time. Further details discussing this control and protection circuitry are described in U.S. Pat. No. 6,516,227, which has been previously incorporated herein by reference.

As briefly discussed above, the portable charger 50 is capable of indicating when the battery 88 of the IPG 14 is fully charged or almost fully charged, and when the portable charger 50 is aligned/misaligned with the IPG 14. To this end, the portable charger 50 comprises charge detection circuitry 98 for detecting an electrical parameter indicative of the charge rate of the IPG 14, and a processor 100 for determining the charging qualities of the IPG 14, and in particular, when the IPG 14 is fully charged and when the portable charger 50 is aligned/misaligned with the IPG 14, based on the detected electrical parameter. The portable charger 50 further comprises memory 102 for storing an electrical parameter threshold value that the processor 100 uses to determine misalignment between the portable charger 50 and IPG 14. The memory 102 also store a computer program used by the processor 100 to perform the functions described below.

In addition to the previously described bar charge indicator 64 (shown in FIG. 3), which visually indicates the charge rate of the IPG 14 to the user, the portable charger 50 also includes an indicator 104 in the form of an audio transducer (speaker), which signals the user with an audible tone when the battery 88 of the IPG 14 is fully charged and when the portable charger 50 is misaligned with the IPG 14. In alternative embodiments, separate indicators can be used to indicate a full charge state and a misalignment condition.

In the illustrated embodiment, the electrical parameter sensed by the charge detection circuitry 98 is a steady-state voltage having a value V1 at the coil 82, which is indicative of the charge rate of the IPG 14. That is, the voltage value V1 (which is dictated by the reflected impedance from the coil 84 of the IPG 14) is inversely proportional to the coupling between the coils 82, 84 of the respective portable charger 50 and IPG 14, and thus, the charge rate of the IPG 14. Thus, as the reflected impedance and thus the voltage value V1 increases, the charge rate decreases, and as reflected impedance and thus the voltage value V1 decreases, the charge rate increases.

The charge detection circuitry 98 also senses the voltage value V1 at the coil 82 to detect when the IPG 14 has been fully charged. In particular, the IPG 14 includes a back telemetry circuit 104, which detects charge completion of the battery 88 and modulates the secondary load of the IPG 14 by changing the rectifier circuitry 86 from a full-wave rectifier into a half-wave rectifier/voltage clamp. This modulation, in turn, suddenly increases the reflected impedance into the coil 82 of the portable charger 50, which suddenly increases the voltage value V1 (e.g., a transient or pulsed component appears in the detected steady-state voltage) detected by the charge detection circuitry 98.

The processor 100 receives the voltage value V1 from the charge detection circuitry 98, and based on this value, operates the bar charge indicator 64 and audio transducer 104 accordingly. In particular, if the voltage value V1 spikes or suddenly increases, the processor 100 determines that the battery 88 of the IPG 14 is fully charged, and prompts the audio transducer 104 (e.g., by sending a signal) to generate an audible tone or series of audible tones (e.g., an ON-OFF beeping sound), thereby alerting the user that the IPG 14 is fully charged.

The processor 100 operates the bar charge indicator 64 to display the proper number of bars in accordance with the charge rate indicated by the voltage value V1. The processor 100 also compares the voltage value V1 to the electrical parameter threshold value (in this case, a voltage threshold value) stored in the memory 102 to determine misalignment between the portable charger 50 and IPG 14. In particular, the processor 100 compares the voltage value V1 with the voltage threshold value stored in the memory 102 to determine whether a misalignment condition has occurred, and operates the audio transducer 104 in a binary fashion, meaning that it only indicates if a particular condition has been satisfied or not satisfied (i.e., misaligned or not misaligned).

Significantly, the voltage threshold value stored in the memory 102 can be varied in order to modify the actual charge rate at which a misalignment condition is deemed to occur. Thus, if the IPG 14 is implanted relatively deep within the patient, the voltage threshold value can be increased, so that the audible misalignment tone does not sound when the charge rate is optimum or otherwise suitable for that implant depth. In contrast, if the IPG 14 is implanted relatively shallow within the patient, the voltage threshold value can be decreased, so that the audible misalignment tone sounds when the charge rate is not optimum or otherwise suitable for that implant depth. Thus, the audible misalignment tone will only sound when the charge rate is sub-optimal for the specific implant depth or orientation.

Adjustment of the voltage threshold value can be accomplished in any one of a variety of manners. For example, in one embodiment, the memory 102 can simply be manually programmed by a clinician with a voltage threshold value suitable for the implant depth. That is, if the IPG 14 has been implanted within the patient relatively deep, the clinician will program the memory 102 with a relatively high voltage threshold value, and if the IPG 14 has been implanted within the patient relatively shallow, the clinician will program the memory 102 with a relatively low voltage threshold value.

In another embodiment, the portable charger 50 can be positioned relative to the IPG 14 until the bar charge indicator 64 indicates a maximum charge rate, at which time the processor 100 (as prompted by the user, e.g., by actuating a button (not shown)) can modify the voltage threshold value to the voltage value V1, which is indicative of the maximum charge rate.

In still another embodiment, the portable charger 50 can be trained over a series of discrete time periods during, e.g., a single session or over multiple sessions. For example, the IPG 14 may be charged by the portable charger 50 over the time periods, during which time the processor 100 can continually determine the maximum voltage value V1, which is indicative of the maximum charge rate, and automatically modify the voltage threshold value to the maximum voltage value V1. Alternatively, the voltage threshold value can be modified to a voltage value just below the maximum voltage value V1, thereby allowing for suitable charge rates less than optimal.

Figure 5:
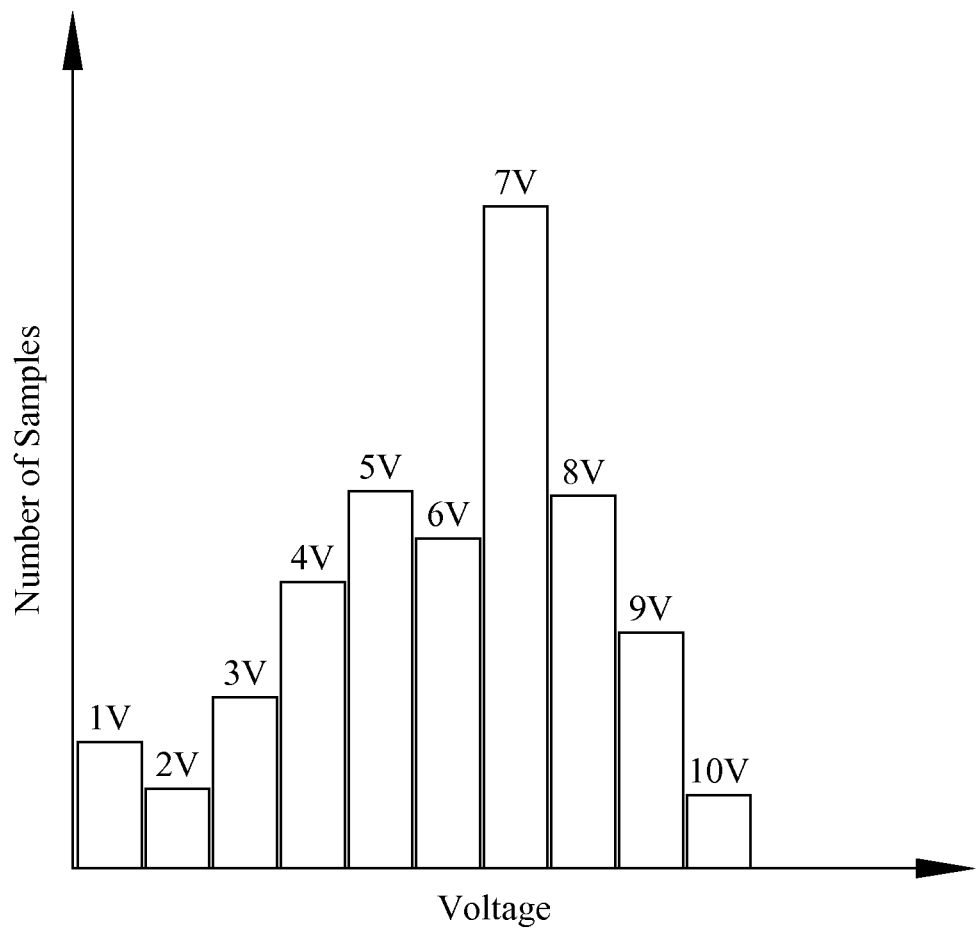
FIG. 5 is an example of a charge rate histogram generated by the external charger of FIG. 4.

Yet another embodiment trades off the ease of positioning the portable charger 50 with the degree of charge rate optimization that the misalignment tone will sound. This embodiment considers not only the maximum charge rate or estimate thereof, but also the histogram of the charge rates across difference charger positions, such that an acceptable zone for locating the portable charger 50 could be maintained automatically. In particular, based on the voltage values V1 detected by the charge detection circuitry 98 over a series of time periods, the processor 100 generates a histogram of voltage values V1, and modifies the voltage threshold value stored in the memory 102 equal to the value of the most common voltage V1, which is indicative of the most common rate used to charge the IPG 14. For example, FIG. 5 illustrates an exemplary histogram that categorizes the voltage values V1 in bins. As there shown, the most common voltage value V1 detected over the 100 time periods was 7V. Thus, in this example, the processor 100 will modify the voltage threshold value to 7V, so that the threshold at which the misalignment tone sounds will be adjusted. Alternatively, the voltage threshold value can be modified to a voltage value just below the most common voltage value V1 (e.g., 6V), thereby allowing for suitable charge rates less than the most common charge rate.

While the modification of a voltage threshold value (or other suitable electrical parameter threshold value) lends itself well to setting the threshold of an audible misalignment tone, thereby ensuring that the patient is alerted only when the portable charger 50 is actually misaligned with the IPG 14, in alternative embodiments, the adjustable voltage threshold value can be used to modify the threshold at which a binary indicator generates a user-discernible signal other than a misalignment signal. For example, the voltage threshold value can correspond to an audio transducer that sounds an alignment tone (i.e., an audible tone that alerts the patient that the portable charger 50 is aligned with the IPG 14), or an indicator that illuminates an alignment light (i.e., a visual signal that alerts the patient that the portable charger 50 is aligned with the IPG 14). In other embodiments, one or more adjustable charge rate threshold values can be used to modify the threshold(s) at which non-binary indicators generate user-discernible signals. For example, the charge rate threshold value(s) can correspond to a bar indicator, such as, e.g., the bar charge indicator 64, such that the thresholds at which the number of bars increases or decreases can be adjusted.

While the sensed electrical parameter that has been described herein as being used as an indication of the charge rate of the IPG 14 is the steady-state voltage value V1 at the coil 82 caused by the unmodulated reflected impedance from the coil 84 of the IPG 14, any electrical parameter indicative of the charge rate can be used as an indication of the charge rate. For example, the charge current of the battery 88 in the IPG 14 is also indicative of the charge rate, with the charge current increasing as the charge rate increases and decreasing as the charge rate decreases. In this case, the value (or some indication) of the battery charge current can be modulated onto the reflected impedance via the back telemetry circuit 104 to provide an indication of the charge rate to the charger 50. The value of the charge current in the modulated signal can then be sensed by the charge detection circuitry 98 of the charger 50 as a modulated voltage, and then, used by the processor 100 to operate the bar charge indicator 64 and audio transducer 104 in the same manner described above.

Notably, due to the constant voltage phase at the end of a charging cycle, the charge current of the battery 88 may not always be indicative of the actual charge rate. That is, the constant voltage phase causes the battery charge current to decrease, regardless of the optimal alignment and spacing between the coils 82, 84. Thus, the battery charge current may decrease even in the presence of a maximum charge rate at the end of the charging cycle. To address this issue, the processor 100 in the charger 50 may normalize the threshold adjustment method or the back telemetry circuit 104 in the IPG 104 may normalize the information modulated onto the reflected impedance to the lower battery charge current during the constant voltage phase.

While the illustrated embodiment has been described as performing the charge rate indication and processing functions in the portable charger 50, it should be appreciated that any of these functions can be performed in the charger base station 52, or even the IPG 14. If the indication function is performed by the IPG 14, the user-discernible signal can take the form of a vibration or a modulated electrical stimulation.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An external charger for an implantable medical device, comprising:
   a source of electrical power;
   an alternating current (AC) coil configured for transcutaneously conveying electrical energy from the electrical power source to charge the implanted medical device;
   a charge strength indicator configured for generating a user-discernible signal at a threshold; and
   a processor configured for increasing the threshold if the medical device is implanted relatively deep, and decreasing the threshold if the medical device is implanted relatively shallow.

2. The external charger of claim 1, further comprising a portable housing containing the electrical power source, AC coil, indicator, detector, and processor.

3. The external charger of claim 1, wherein the indicator is an audio transducer.

4. The external charger of claim 1, wherein the indicator is a binary indicator.

5. The external charger of claim 1, wherein the indicator is one of an alignment indicator and a misalignment indicator.

6. The external charger of claim 1, wherein the processor is configured for adjusting the threshold in response to a user input.

7. The external charger of claim 1, further comprising a detector configured for detecting an electrical parameter, wherein the processor configured for adjusting the threshold based on the detected electrical parameter.

8. The external charger of claim 7, wherein the processor is configured for automatically adjusting the threshold in response to the detection of the electrical parameter.

9. The external charger of claim 7, wherein the electrical parameter is a steady-state charging voltage.

10. The external charger of claim 7, wherein the electrical parameter indicates a rate at which the implanted medical device is charged by the electrical energy.

11. An external charger for an implantable medical device, comprising:
    a source of electrical power;
    an alternating current (AC) coil configured for transcutaneously conveying electrical energy from the electrical power source to charge the implanted medical device;
    a user interface configured for receiving a user prompt;
    a charge strength indicator configured for generating a user-discernible signal; and
    a processor configured for adjusting a threshold at which the charge strength indicator generates a user-discernible signal in response to the user prompt.

12. The external charger of claim 11, further comprising a portable housing containing the electrical power source, AC coil, indicator, detector, and processor.

13. The external charger of claim 11, wherein the indicator is an audio transducer.

14. The external charger of claim 11, wherein the indicator is a binary indicator.

15. The external charger of claim 11, wherein the indicator is one of an alignment indicator and a misalignment indicator.

16. The external charger of claim 11, wherein the user interface comprises a button, and the user prompt is an actuation of the button.

17. The external charger of claim 11, further comprising:
    a detector configured for detecting an electrical parameter; and
    a non-binary indicator configured for indicating a rate at which the implanted medical device is charged by the electrical energy based on the detected electrical parameter.

18. The external charger of claim 17, wherein the processor is configured for adjusting the threshold to the value of the detected electrical parameter.

19. An external charger for an implantable medical device, comprising:
    a source of electrical power;
    an alternating current (AC) coil configured for transcutaneously conveying electrical energy from the electrical power source to charge the implanted medical device;
    a charge strength indicator configured for generating a user-discernible signal;
    a detector configured for detecting an electrical parameter during a series of discrete time periods; and
    a processor configured for determining the value of the detected electrical parameter indicating a most common charge rate during the discrete time periods, and adjusting a threshold at which the charge strength indicator generates the user-discernible signal based on the determined electrical parameter value.

20. The external charger of claim 19, further comprising a portable housing containing the electrical power source, AC coil, indicator, detector, and processor.

21. The external charger of claim 19, wherein the indicator is an audio transducer.

22. The external charger of claim 19, wherein the indicator is a binary indicator.

23. The external charger of claim 19, wherein the indicator is one of an alignment indicator and a misalignment indicator.

24. The external charger of claim 19, wherein the processor is further configured for generating an electrical parameter histogram over the discrete time periods, and determining the detected electrical parameter value indicating the most common charge rate from the electrical parameter histogram.

25. The external charger of claim 19, wherein the processor is configured for adjusting the threshold to a value equal to the detected electrical parameter value indicating the most common charge rate.

26. The external charger of claim 19, wherein the processor is configured for adjusting the threshold to a value less than the detected electrical parameter value indicating the most common charge rate.

* * * * *